(12) United States Patent
Marcovecchio

(10) Patent No.: US 7,039,463 B2
(45) Date of Patent: *May 2, 2006

(54) DISCRIMINATION OF SUPRAVENTRICULAR TACHYCARDIA AND VENTRICULAR TACHYCARDIA EVENTS

(75) Inventor: Alan F. Marcovecchio, Minneapolis, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 111 days.

This patent is subject to a terminal disclaimer.

(21) Appl. No.: 10/731,223

(22) Filed: Dec. 9, 2003

(65) Prior Publication Data

US 2004/0116972 A1 Jun. 17, 2004

Related U.S. Application Data

(60) Continuation of application No. 09/990,151, filed on Nov. 21, 2001, now Pat. No. 6,687,540, which is a division of application No. 09/666,868, filed on Sep. 20, 2000, now Pat. No. 6,484,055, which is a division of application No. 09/267,307, filed on Mar. 12, 1999, now Pat. No. 6,223,078.

(51) Int. Cl.
*A61N 1/362* (2006.01)
(52) U.S. Cl. .................................................... 607/14
(58) Field of Classification Search ............ 607/4, 607/5, 9, 14; 600/508, 515, 518
See application file for complete search history.

(56) References Cited

U.S. PATENT DOCUMENTS

| | | | |
|---|---|---|---|
| 4,023,564 A | 5/1977 | Valiquette et al. ...... | 128/206 A |
| 4,336,810 A | 6/1982 | Anderson et al. | |
| 4,531,527 A | 7/1985 | Reinhold, Jr. et al. ...... | 128/696 |
| 4,583,553 A | 4/1986 | Shah et al. .................. | 128/704 |
| 4,721,114 A | 1/1988 | DuFault et al. ............. | 128/696 |
| 4,830,006 A | 5/1989 | Haluska et al. | |
| 4,838,278 A | 6/1989 | Wang et al. | |
| 4,924,875 A | 5/1990 | Chamoun .................... | 128/696 |
| 4,940,054 A | 7/1990 | Grevis et al. | |

(Continued)

FOREIGN PATENT DOCUMENTS

DE    4405827    6/1995

(Continued)

OTHER PUBLICATIONS

Chen, Victor T., "Method and Apparatus for Using Atrial Discrimination Algorithms to Determine Optimal Pacing Therapy and Therapy Timing", U.S. Appl. No. 09/712,600, filed Nov. 14, 2000, 34 pgs.

(Continued)

*Primary Examiner*—George R. Evanisko
(74) *Attorney, Agent, or Firm*—Schwegman, Lundberg, Woessner & Kluth, P.A.

(57) ABSTRACT

A method and system for discrimination of supraventricular tachycardia and ventricular tachycardia events. Morphological features points are extracted from normal sinus rhythm (NSR) complexes and used to generate a NSR template. A numerical convolution is performed using the NSR template and the feature points for each sensed NSR to give a NSR filter output. Using a plurality of NSR complexes, a median NSR filter output template is determined, where the median NSR filter output template has a median value for each value in the NSR filter output. The median NSR filter output template is then used during a tachycardia event to distinguish tachycardia events as either ventricular tachycardia events or supraventricular tachycardia events.

20 Claims, 8 Drawing Sheets

U.S. PATENT DOCUMENTS

| | | | |
|---|---|---|---|
| 5,000,189 A | 3/1991 | Throne et al. | 128/702 |
| 5,014,284 A | 5/1991 | Langer et al. | 375/30 |
| 5,020,540 A | 6/1991 | Chamoun | 128/696 |
| 5,107,850 A | 4/1992 | Olive | 128/705 |
| 5,109,842 A | 5/1992 | Adinolfi | 128/419 D |
| 5,139,028 A | 8/1992 | Steinhaus et al. | 128/697 |
| 5,156,148 A | 10/1992 | Cohen | 128/419 PG |
| 5,184,615 A | 2/1993 | Nappholz et al. | 128/419 PG |
| 5,193,535 A | 3/1993 | Bardy et al. | |
| 5,193,550 A | 3/1993 | Duffin | 129/697 |
| 5,215,098 A | 6/1993 | Steinhaus et al. | 128/702 |
| 5,217,021 A | 6/1993 | Steinhaus et al. | |
| 5,240,009 A | 8/1993 | Williams | 128/702 |
| 5,247,021 A | 9/1993 | Fujisawa et al. | 525/254 |
| 5,255,186 A | 10/1993 | Steinhaus et al. | 364/413 |
| 5,269,301 A | 12/1993 | Cohen | 607/6 |
| 5,271,411 A | 12/1993 | Ripley et al. | 128/702 |
| 5,273,049 A | 12/1993 | Steinhaus et al. | 128/696 |
| 5,280,792 A | 1/1994 | Leong et al. | 128/702 |
| 5,292,348 A | 3/1994 | Saumarez et al. | 607/5 |
| 5,311,874 A | 5/1994 | Baumann et al. | 128/705 |
| 5,312,445 A | 5/1994 | Nappholz et al. | 607/9 |
| 5,313,953 A | 5/1994 | Yomtov et al. | 128/696 |
| 5,330,504 A | 7/1994 | Somerville et al. | 607/5 |
| 5,331,966 A | 7/1994 | Bennett et al. | 128/696 |
| 5,342,402 A | 8/1994 | Olson et al. | 607/5 |
| 5,350,406 A | 9/1994 | Nitzsche et al. | 607/14 |
| 5,356,425 A | 10/1994 | Bardy et al. | |
| 5,360,436 A | 11/1994 | Alt et al. | 607/18 |
| 5,366,487 A | 11/1994 | Adams et al. | |
| 5,388,578 A | 2/1995 | Yomtov et al. | 128/642 |
| 5,400,795 A | 3/1995 | Murphy et al. | 128/702 |
| 5,400,796 A | 3/1995 | Wecke | |
| 5,411,031 A | 5/1995 | Yomtov | 128/706 |
| 5,421,830 A | 6/1995 | Epstein et al. | 607/30 |
| 5,447,519 A | 9/1995 | Peterson | 607/5 |
| 5,447,524 A | 9/1995 | Alt | 607/19 |
| 5,456,261 A | 10/1995 | Luczyk | 128/702 |
| 5,458,623 A | 10/1995 | Lu et al. | 607/28 |
| 5,478,807 A | 12/1995 | Cronin et al. | 514/12 |
| 5,509,927 A | 4/1996 | Epstein et al. | 607/32 |
| 5,520,191 A | 5/1996 | Karlsson et al. | 128/702 |
| 5,542,430 A | 8/1996 | Farrugia et al. | 128/705 |
| 5,545,186 A | 8/1996 | Olson et al. | |
| 5,549,641 A | 8/1996 | Ayers et al. | 607/4 |
| 5,622,178 A | 4/1997 | Gilham | 128/696 |
| 5,634,468 A | 6/1997 | Platt et al. | 128/696 |
| 5,645,070 A | 7/1997 | Turcott | 128/702 |
| 5,676,153 A | 10/1997 | Smith et al. | |
| 5,682,900 A | 11/1997 | Arand et al. | 600/517 |
| 5,683,425 A | 11/1997 | Hauptmann | 607/9 |
| 5,687,737 A | 11/1997 | Branham et al. | 128/710 |
| 5,712,801 A | 1/1998 | Turcott | 364/550 |
| 5,713,367 A | 2/1998 | Arnold et al. | 128/704 |
| 5,724,985 A | 3/1998 | Snell et al. | 128/697 |
| 5,730,141 A | 3/1998 | Fain et al. | |
| 5,730,142 A | 3/1998 | Sun et al. | 128/705 |
| 5,755,736 A | 5/1998 | Gillberg et al. | |
| 5,755,737 A | 5/1998 | Prieve et al. | |
| 5,755,739 A | 5/1998 | Sun et al. | 607/14 |
| 5,759,158 A | 6/1998 | Swanson | 600/508 |
| 5,772,604 A | 6/1998 | Langberg et al. | 200/518 |
| 5,778,881 A | 7/1998 | Sun et al. | 128/696 |
| 5,779,645 A | 7/1998 | Olson et al. | 600/518 |
| 5,782,888 A | 7/1998 | Sun et al. | 607/27 |
| 5,792,065 A | 8/1998 | Xue et al. | 600/516 |
| 5,792,193 A | 8/1998 | Stoop | |
| 5,795,303 A | 8/1998 | Swanson et al. | 600/509 |
| 5,797,399 A | 8/1998 | Morris et al. | 128/705 |
| 5,797,849 A | 8/1998 | Vesely et al. | 600/461 |
| 5,814,081 A | 9/1998 | Ayers et al. | |
| 5,817,133 A | 10/1998 | Houben | 607/9 |
| 5,819,007 A | 10/1998 | Elghazzawi | 395/51 |
| 5,819,741 A | 10/1998 | Karlsson | 600/523 |
| 5,836,975 A | 11/1998 | DeGroot | |
| 5,848,972 A | 12/1998 | Triedman et al. | 600/508 |
| 5,857,977 A | 1/1999 | Caswell et al. | |
| 5,858,977 A | 1/1999 | Aukerman et al. | 514/12 |
| 5,873,897 A | 2/1999 | Armstrong et al. | |
| 5,897,575 A | 4/1999 | Wickham | |
| 5,944,744 A | 8/1999 | Paul et al. | |
| 5,951,592 A | 9/1999 | Murphy | |
| 5,978,707 A | 11/1999 | Krig et al. | |
| 5,991,657 A | 11/1999 | Kim | |
| 6,041,251 A | 3/2000 | Kim et al. | |
| 6,052,620 A | 4/2000 | Gillberg et al. | |
| 6,076,014 A | 6/2000 | Alt | 607/4 |
| 6,096,061 A | 8/2000 | Alt et al. | 607/4 |
| 6,179,865 B1 | 1/2001 | Hsu et al. | |
| 6,181,364 B1 | 1/2001 | Ford | 348/5.5 |
| 6,212,428 B1 | 4/2001 | Hsu et al. | |
| 6,223,078 B1 * | 4/2001 | Marcovecchio | 607/5 |
| 6,249,699 B1 | 6/2001 | Kim | |
| 6,266,554 B1 | 7/2001 | Hsu et al. | 600/515 |
| 6,275,732 B1 | 8/2001 | Hsu et al. | 607/14 |
| 6,308,095 B1 | 10/2001 | Hsu et al. | 600/518 |
| 6,312,388 B1 | 11/2001 | Marcovecchio et al. | 600/508 |
| 6,314,321 B1 | 11/2001 | Morris | 607/9 |
| 6,351,669 B1 | 2/2002 | Hartley et al. | 607/5 |
| 6,353,759 B1 | 3/2002 | Hartley et al. | 607/9 |
| 6,411,848 B1 | 6/2002 | Kramer et al. | 607/9 |
| 6,430,435 B1 | 8/2002 | Hsu et al. | 600/518 |
| 6,430,438 B1 | 8/2002 | Chen et al. | 607/5 |
| 6,434,417 B1 | 8/2002 | Lovett | 600/509 |
| 6,438,410 B1 | 8/2002 | Hsu et al. | 600/516 |
| 6,442,425 B1 | 8/2002 | Alt | 607/4 |
| 6,449,503 B1 | 9/2002 | Hsu | 600/518 |
| 6,456,871 B1 | 9/2002 | Hsu et al. | |
| 6,484,055 B1 * | 11/2002 | Marcovecchio | 607/5 |
| 6,501,988 B1 | 12/2002 | Kramer et al. | 607/9 |
| 6,512,951 B1 | 1/2003 | Marcovecchio et al. | 607/5 |
| 6,526,313 B1 | 2/2003 | Sweeney et al. | |
| 6,687,540 B1 * | 2/2004 | Marcovecchio | 607/5 |
| 6,708,058 B1 | 3/2004 | Kim et al. | |
| 6,728,572 B1 | 4/2004 | Hsu et al. | |
| 6,889,081 B1 | 5/2005 | Hsu | |
| 2002/0032469 A1 | 3/2002 | Marcovecchio | |
| 2002/0049474 A1 | 4/2002 | Marcovecchio et al. | |
| 2002/0091333 A1 | 7/2002 | Hsu et al. | |
| 2002/0107552 A1 | 8/2002 | Krig et al. | |
| 2002/0183637 A1 | 12/2002 | Kim et al. | |
| 2002/0183639 A1 | 12/2002 | Sweeney et al. | |
| 2002/0198461 A1 | 12/2002 | Hsu et al. | |
| 2003/0060849 A1 | 3/2003 | Hsu | |
| 2003/0109792 A1 | 6/2003 | Hsu | |
| 2003/0120316 A1 | 6/2003 | Spinelli et al. | |
| 2003/0181818 A1 | 9/2003 | Kim et al. | |
| 2004/0015090 A1 | 1/2004 | Sweeney et al. | |
| 2004/0093035 A1 | 5/2004 | Schwartz et al. | |
| 2004/0116972 A1 | 6/2004 | Marcovecchio | |
| 2004/0127806 A1 | 7/2004 | Sweeney | |
| 2004/0176694 A1 | 9/2004 | Kim et al. | |
| 2005/0010257 A1 | 1/2005 | Lincoln et al. | |
| 2005/0159781 A1 | 7/2005 | Hsu et al. | |

FOREIGN PATENT DOCUMENTS

| | | |
|---|---|---|
| EP | 0469817 A2 | 2/1992 |
| EP | 0506230 A1 | 9/1992 |
| EP | 0554208 | 8/1993 |
| EP | 0711531 | 5/1996 |
| EP | 0776631 | 11/1996 |
| EP | 0848965 | 6/1998 |
| WO | WO-93/02746 | 2/1993 |

| | | |
|---|---|---|
| WO | WO-97/39681 | 4/1996 |
| WO | WO-0126733 A1 | 4/2001 |

OTHER PUBLICATIONS

Jenkins, "Diagnosis of Atrial Fibrillation Using Electrogram from Chronic Leads: Evaluation of Computer Algorithm", *PACE*, 11, (1988), pp. 622-631.

Jung, J., et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998), pp. 689-695.

Li, Dan, "Method and Apparatus for Rate-Dependent Morphology-Based Cardiac Arrhythmia Classification", U.S. Appl. No. 11/151,567, filed on Jun. 13, 2005, 53 pgs.

Li, Dan, "Methods and Apparatuses for Cardiac Arrhythmia Classification Using Morphology Stablilty", U.S. Appl. No. 11/038,996, filed Jan. 20, 2005, 74 pgs.

Morris, Milton M., "Detection of Atrial Arrhythmia for Cardiac Rhythm Management by Implantable Devices", *Journal of Electrocardiology*, vol. 33, (2000), 133-139.

Swiryn, S., et al., "Detection of Atrial Fibrillation by Pacemakers and Antiarrhythmic Devices", *Nonpharmacological Management of Atrial Fibrillation*, Chapter 21, Futura Publishing Co, Inc. Armonk, NY, (1997), pp. 309-318.

Thompson, Julie, "Template Based AV/VA Interval Comparison for the Discrimination of Cardiac Arrhythmia", U.S. Appl. No. 10/844,475, filed May 12, 2004, 33 pgs.

Zhang, Yi, "Methods and Apparatuses for Arrhythmia Detection and Classification Using Wireless ECG", U.S. Appl. No. 10/975,166, filed Oct. 28, 2004, 69 pgs.

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999), 1039-1046.

Ellenbogen, Kenneth A., "Cardiac Pacing", *Cambridge, Mass., USA: Blackwell Science*, 2nd ed., (1996), 311-312 & 435-437.

Grady, Thomas A., et al., "Prognostice Significance of Exercise-Induced Left Bundle-Branch Block", *JAMA*, vol. 279, No. 2, Jan. 14, 1998, 153-156.

IEEE, "Microcomputer-Based Telemetry System for ECG Monitoring", *IEEE Proc. of the Ann. Int'l Conf. of the Engineering in Medicine and Biology Society*, vol. Conf. 9, XP000015425, (1987), 1492-193.

Kinoshita, Shinji, et al., "Transient Disapperance of Complete Right Bundle Branch (BBB) During Exercise", *Journal of Electrocardiology*, vol. 29, No. 3, 1996, (1996), 255-256.

Smith, V., "Systems, Devices and Methods For Tachyarrythmia Discrimination or Therapy Decisions", U.S. Appl. No. 10/897,365, filed Jul. 22, 2004, 38 pgs.

\* cited by examiner

DISCRIMINATION OF SUPRAVENTRICULAR TACHYCARDIA AND VENTRICULAR TACHYCARDIA EVENTS

CROSS-REFERENCE TO RELATED APPLICATIONS

This application is a continuation of U.S. patent application Ser. No. 09/990,151, filed Nov. 21, 2001, now U.S. Pat. No. 6,687,540 which is a division of U.S. patent application Ser. No. 09/666,868, filed on Sep. 20, 2000, now issued as U.S. Pat. No. 6,484,055, which is a division of U.S. patent application Ser. No. 09/267,307, filed on Mar. 12, 1999, now issued as U.S. Pat. No. 6,223,078, the specifications of which are hereby incorporated by reference.

FIELD OF THE INVENTION

This invention relates generally to medical devices, and more particularly to a system and method for discriminating supraventricular tachycardia from ventricular tachycardia during a tachycardia event.

BACKGROUND

The heart is generally divided into four chambers, the left and right atrial chambers and the left and right ventricular chambers. As the heart beats, the atrial chambers and the ventricular chambers go through a cardiac cycle. The cardiac cycle consists of one complete sequence of contraction and relaxation of the chambers of the heart. The terms systole and diastole are used to describe the contraction and relaxation phases the chambers of the heart experience during a cardiac cycle. In systole, the ventricular muscle cells contract to pump blood through the circulatory system. During diastole, the ventricular muscle cells relax, causing blood from the atrial chamber to fill the ventricular chamber. After the period of diastolic filling, the systolic phase of a new cardiac cycle is initiated.

Through the cardiac cycle, the heart pumps blood through the circulatory system. Effective pumping of the heart depends upon five basic requirements. First, the contractions of cardiac muscle must occur at regular intervals and be synchronized. Second, the valves separating the chambers of the heart must fully open as blood passes through the chambers. Third, the valves must not leak. Fourth, the contraction of the cardiac muscle must be forceful. Fifth, the ventricles must fill adequately during diastole.

When the contractions of the heart are not occurring at regular intervals or are unsynchronized the heart is said to be arrhythmic. During an arrhythmia, the heart's ability to effectively and efficiently pump blood is compromised. Many different types of arrhythmias have been identified. Arrhythmias can occur in either the atrial chambers or in the ventricular chambers of the heart.

Ventricular fibrillation is an arrhythmia that occurs in the ventricle chambers of the heart. In ventricular fibrillation, various areas of the ventricle are excited and contract asynchronously. During ventricular fibrillation the heart fails to pump blood. Since no blood is pumped during ventricular fibrillation, the situation is fatal unless quickly corrected by cardiac conversion. Ventricular tachycardia is another arrhythmia that occurs in the ventricular chambers of the heart. Ventricular tachycardia is a very serious condition. Ventricular tachycardias are typified by ventricular rates between 120–250 and are caused by disturbances (electrical or mechanical) within the ventricles of the heart. During a ventricular tachycardia, the diastolic filling time is reduced and the ventricular contractions are less synchronized and therefore less effective than normal. Ventricular tachycardias must be treated quickly in order to prevent the tachycardia from degrading into a life threatening ventricular fibrillation.

Arrhythmias that occur in the atrial chambers of the heart are referred to generally as supraventricular tachycardias. Supraventricular tachycardias include atrial tachycardias, atrial flutter and atrial fibrillation. During certain supraventricular tachycardias, aberrant cardiac signals from the atria drive the ventricles at a very rapid rate. Such a situation occurs during paroxysmal atrial tachycardia. This condition begins abruptly, lasts for a few minutes to a few hours, and then, just as abruptly, disappears and the heart rate reverts back to normal.

Cardioverter-defibrillators, such as implantable cardioverter-defibrillators (ICDs), have been shown to be effective in reducing the incidence of sudden cardiac death. Sudden cardiac death is typically caused by either ventricular tachycardia or ventricular fibrillation. Cardioverter-defibrillator systems operate by sensing and analyzing cardiac signals and applying electrical energy to the heart when either a ventricular tachycardia or ventricular fibrillation is detected. One common way cardioverter-defibrillators detect cardiac arrhythmias is to sense and analyze the rate of ventricular contractions. When the ventricular rate exceeds a programmed threshold value, the cardioverter-defibrillator applies electrical energy in one or more specific patterns to treat either the ventricular tachycardia or ventricular fibrillation.

Rapid ventricular rhythms, however, can occur in the presence of a supraventricular tachycardia. As previously mentioned, one example is during paroxysmal atrial tachycardia. In this situation, treating the ventricles with electrical energy is inappropriate as the treatment does not address the precipitating factor of the rapid ventricular rate. Therefore, a need exists for reliably assessing and determining the origin of a rapid ventricular rate. By reliably discriminating the origin of the rapid ventricular rate, more appropriate and effective therapies can be applied to treat the heart.

SUMMARY OF THE INVENTION

The present subject matter discloses a method and a system for discriminating, or classifying supraventricular tachycardias (SVT) from malignant ventricular tachycardias (VT) during a tachycardia event. In one embodiment, the present subject matter is implemented in an implantable cardioverter defibrillator. By using the method of the present subject matter, the implantable defibrillator assesses and determines the origin of a rapid ventricular rate, allowing the implantable defibrillator to reduce the number of inappropriate therapies delivered to the heart.

In one embodiment, QRS-complexes are sensed during normal sinus rhythm (NSR). A plurality of feature points are located on the sensed NSR QRS-complexes based on morphological features of the individual NSR QRS-complexes. The plurality of feature points from the NSR QRS-complexes are then used to determine a NSR template. In one embodiment, a plurality of NSR QRS-complexes are used to determine the NSR template.

In one embodiment, the NSR template includes a median value for each of the plurality of feature points taken along the NSR QRS-complex. A numerical convolution is then preformed on the values of the NSR template. A numerical convolution is also preformed on the plurality of feature points for each of the plurality of the NSR QRS-complexes.

This process gives a NSR filter output for each of the NSR QRS-complexes. Using the NSR filter output for each NSR QRS-complex, a median NSR filter output template is determined. In one embodiment, the median NSR filter output template includes the median values of the NSR filter output values for each NSR QRS-complex.

Once the median NSR filter output template has been determined, the system senses for the occurrence of a tachycardia event. When a tachycardia event is detected, the system senses the tachycardia complexes. In one embodiment, QRS-complexes are extracted, or sampled, from the tachycardia complexes in the sensed signals. The plurality of feature points are then located in the QRS-complexes. The feature points located in the QRS-complexes during the tachycardia event are based on morphological features of the QRS-complex. In one embodiment, the morphological features taken from the QRS-complex during the tachycardia episode are from the same relative position as the morphological features taken along the NSR QRS-complex.

A tachycardia complex output is then determined by performing a numerical convolution of the median NSR filter output template with the plurality of feature points from a QRS-complex of a tachycardia complex sensed during the tachycardia event. The differences between the values of the tachycardia complex output and the median NSR filter output template are summed to give a sum of residual value. The sum of residual (SOR) value is then compared to a sum of residual (SOR) threshold value, and when the SOR value is greater than or equal to the SOR threshold value the tachycardia complex is classified as a ventricular tachycardia complex. When the SOR value is less than the SOR threshold value the tachycardia complex is classified as a supraventricular tachycardia complex. When the number of tachycardia complexes classified as either ventricular tachycardia complexes or supraventricular tachycardia complexes exceeds a predetermined threshold value, the tachycardia event is classified as the tachycardia event that exceeded the threshold value (i.e., as either a ventricular tachycardia or a supraventricular tachycardia).

These and other features and advantages of the invention will become apparent from the following description of the preferred embodiments of the invention.

DETAILED DESCRIPTION

Figure 1:
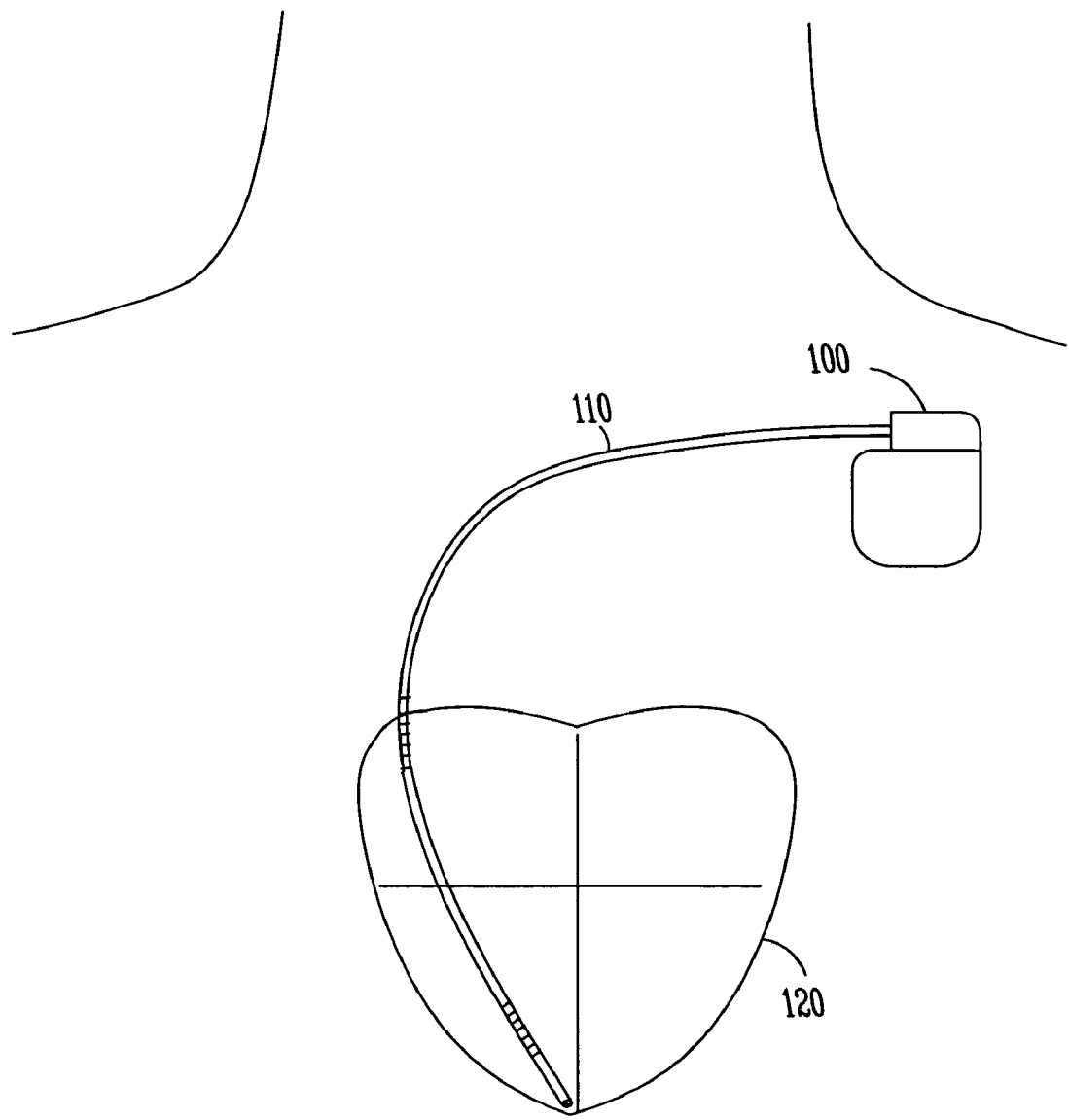
FIG. 1 is a schematic of an implantable medical device.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments illustrated herein are demonstrated in an implantable cardiac defibrillator (ICD), which may include numerous defibrillation, pacing, and pulse generating modes known in the art. However, these embodiments are illustrative of some of the applications of the present system, and are not intended in an exhaustive or exclusive sense. The concepts described herein can be used in a variety of applications which will be readily appreciated by those skilled in the art upon reading and understanding this description. For example, the present system is suitable for implementation in a variety of implantable and external devices.

As discussed above, ICDs can deliver inappropriate therapy to the ventricles of the heart. One example is when a supraventricular tachycardia causes a rapid ventricular rate. The ICD senses the rapid ventricular rate and responds by treating the heart (i.e., delivering electrical energy to the ventricles) as if a ventricular tachycardia were occurring. However, when the cause of the rapid ventricular rate is a supraventricular tachycardia treating the ventricles is inappropriate as the therapy is not directed at the source of the arrhythmia. Looking at it another way, the ICD is attempting to treat the symptoms, not the cause of the rapid ventricular rate.

The present subject matter allows for the origin, or the source, of a rapid ventricular rate to be distinguished. In one embodiment, the present subject matter distinguishes the origin of a ventricular tachycardia as either the result of a supraventricular tachycardia (i.e., an arrhythmia in the atria is driving the ventricles at a rapid rate) or the result of a disturbance in the ventricles (i.e., a ventricular tachycardia).

Rapid ventricular rates can include ventricular rates that are between 100-250 beats per minute, as are typical during ventricular tachycardia. Ventricular rates of greater than 250 beats per minute are also considered to be within the present subject matter.

The present subject matter utilizes sensed cardiac complexes in determining, or distinguishing, the source of rapid ventricular rates. Cardiac complexes include the electrical excitatory impulses, or action potentials, that are sensed from the heart is it goes through the cardiac cycle. In one embodiment, the sensed cardiac complexes are electrocardiogram signals sensed from the beating heart. Major features of an electrocardiogram signal include the P-wave, the QRS-complex and the T-wave which are caused by the atrial depolarization, the ventricular depolarization and the ventricular repolarization, respectively.

In one embodiment, cardiac complexes are sensed and analyzed using an ICD system. In one embodiment, the ICD system uses a transvenous lead system to allow sensing of the cardiac action potentials. The transvenous lead system can include a rate-sensing electrode and at least one defibrillation electrode positioned on the transvenous lead. Cardiac action potentials sensed using defibrillation electrodes are typically referred to as far-field signals (or morphology signals) and cardiac action potentials sensed using rate sensing, or pacing, electrodes are typically referred to as near-field signals (or rate signals).

In one embodiment, the rate-sensing electrode is a pacing tip electrode positioned at the distal end of the transvenous lead system. Other types of rate sensing electrodes are also considered appropriate to use with the present subject matter. Examples of other types of rate sensing electrodes include ring electrodes, both annular and semi-annular, as are known in the art. Rate sensing using the transvenous lead system can also be accomplished either through unipolar or bipolar sensing methods, as are known.

In one embodiment, the transvenous lead system can have a single defibrillation electrode. When a single defibrillation electrode is present, the ICD uses unipolar sensing and defibrillation, as is known. In one embodiment, a transvenous catheter with a single defibrillation electrode is implanted with the rate sensing electrode and the defibrillation electrode positioned within the right ventricular chamber of the heart. In an alternative embodiment, the transvenous lead can have two, or more, defibrillation electrodes. When two defibrillation electrodes are present, the ICD system can preform bipolar sensing the cardiac action potentials. In bipolar sensing, cardiac action potentials are sensed between the two defibrillation electrodes, and defibrillation electrical shocks are delivered between the two defibrillation electrodes. The ICD system of the present subject matter can also use endocardial and patch electrodes as are known.

In one embodiment, the ICD employs an single body lead catheter sold under the trademark ENDOTAK (Cardiac Pacemaker, Inc./Guidant Corporation, St. Paul, Minn.) having a pacing tip electrode and two defibrillation coil electrodes. One example of such a system is shown in FIG. 1. ICD 100 is coupled to catheter 110, which is implanted to receive signals from heart 120. The catheter 110 also may be used for transmission of pacing and/or defibrillation signals to the heart 120. In an alternative embodiment, a three defibrillation electrode system is employed, wherein the housing of the implantable system is used as a third defibrillation electrode.

In one example, the ICD 100 senses cardiac signals from the heart 120. When the ICD 100 detects the occurrence of an arrhythmic event, the ICD 100 analyzes the sensed arrhythmic complexes (i.e., the cardiac signals) of the arrhythmic event. During the analysis, the ICD compares the sensed arrhythmic complexes to cardiac signals sensed and recorded during the patient's normal sinus rhythm. Based on the comparison, the ICD 100 is able to distinguish SVT events from VT events and, depending upon the ICD's classification of the arrhythmic event, to provide appropriate therapy to treat the heart 120.

Figure 2:
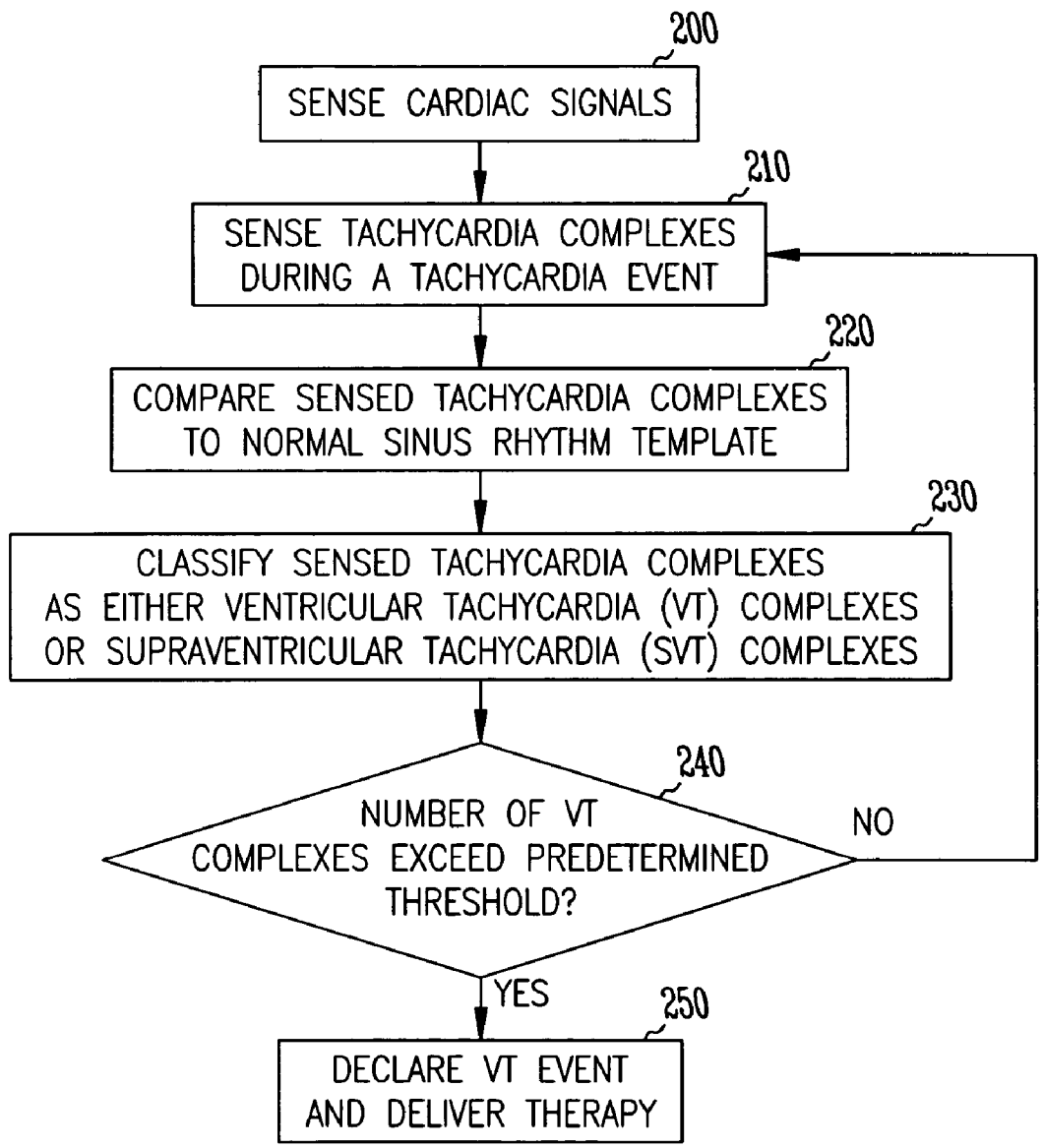
FIG. 2 is a flow chart illustrating one embodiment of the present subject matter.

FIG. 2 shows another embodiment of a system for distinguishing SVT events from VT events during a tachycardia event. At 200, the system senses cardiac signals representative of electrical cardiac activity. At 210, the system analyzes the sensed cardiac signals to detect the occurrence of a tachycardia event in the heart. In one embodiment, the tachycardia event are ventricular arrhythmic events.

When tachycardia event is detected at 210, the system continues to sense the tachycardia complexes. At 220, the sensed tachycardia complexes are then compared to a template in order to determine the classification of the sensed tachycardia complex. In one embodiment, the template is determined from cardiac complexes sensed during normal sinus rhythm. For example, features from the cardiac complexes sensed during normal sinus rhythm are used to create a normal sinus rhythm template. Features from the tachycardia complexes sensed during the tachycardia event are then compared to the normal sinus rhythm template. In one embodiment, the features from the sensed tachycardia complexes correspond to the features taken from the cardiac complexes sensed during normal sinus rhythm. In other words, features taken from the tachycardia complexes are from the same relative location as those taken from the normal sinus rhythm cardiac complexes.

In one embodiment, the comparison of the sensed tachycardiac complexes and the normal sinus rhythm template at 220 determines how similar or dissimilar the sensed tachycardiac complexes are from the patient's normal sinus rhythm complexes. Based on the comparison, the system at 230 then classifies the sensed tachycardiac complexes as either ventricular tachycardiac signals or supraventricular tachycardia signals. As the tachycardiac complexes are classified, the system counts the occurrence and the classification of each tachycardiac complex. At 240, the system then determines whether the number of sensed ventricular tachycardia complexes has exceeded a predetermined threshold value. If the threshold has been exceeded, the system proceeds to 250 where a ventricular tachycardia event is declared and therapy to treat the ventricular tachycardia is delivered to the patient's heart. If the threshold has not been exceeded, the system returns to 210, where additional cardiac complexes are sensed and classified by the system.

Figure 3:
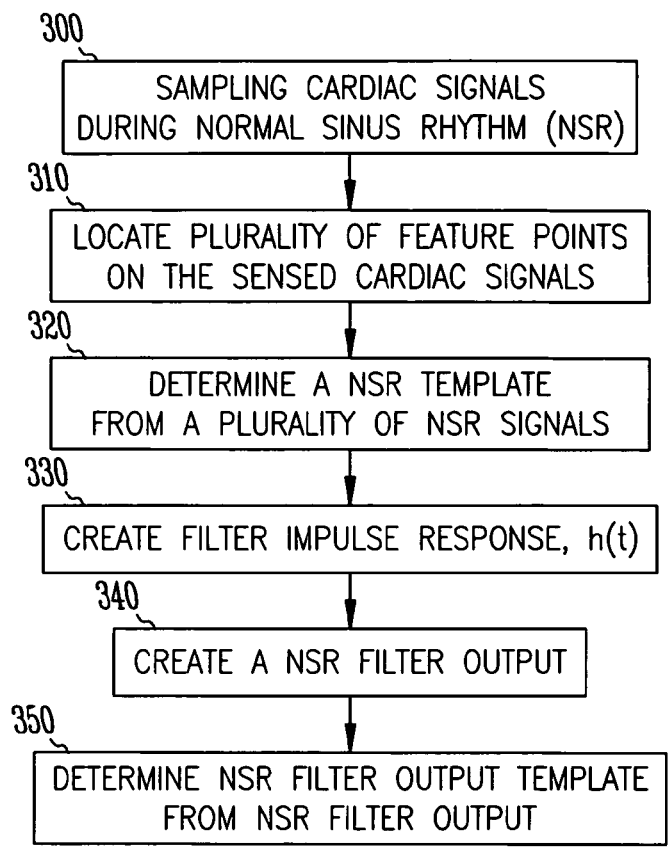
FIG. 3 is a flow chart illustrating one embodiment of the present subject matter.

FIG. 3 shows an embodiment for determining a normal sinus rhythm (NSR) template. At 300, the system senses cardiac complexes during normal sinus rhythm (NSR). In one embodiment, the NSR complexes are sensed and recorded using the ICD under the supervision of the patient's attending physician. In one embodiment, the system samples, or senses, QRS-complexes of the NSR complexes.

As each QRS-complex is sensed it is isolated, or windowed, for analysis. At 310, a plurality of feature points are located on the QRS-complex. In one embodiment, the plurality of feature points are morphological features of the QRS-complex. For example, morphological features extracted from the QRS-complexes include the amplitude values of peaks and valleys (or maxima and minima) acquired by a process called feature extraction. During feature extraction, each NSR complex is isolated according to a known morphological template. In one embodiment, the morphological template operates to detect the activation of an heart beat (such as the occurrence of an R-wave), at which point the electronic control circuitry of the implantable medical device analyzes the complex associated with the signal indicating the activation of the heart beat. In one embodiment, a threshold value or a detection criterion is used to indicate the activation of the heart beat. Once a heart beat has been detected, the feature extraction derives the plurality of feature points from the morphological features of the NSR complex. The extracted feature points for each NSR complex create a vector. In one embodiment, the vector includes a set of numbers, where each number is associated with a particular morphological point along the sensed NSR complex. Other types of features known in the art can also be extracted and used in developing the NSR template.

Figure 4:
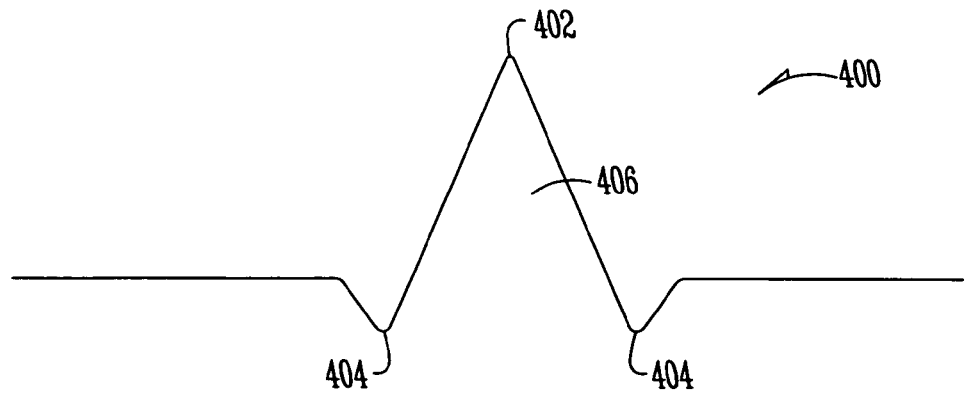
FIG. 4 shows one embodiment of an electrocardiogram of a normal sinus rhythm complex.

In one embodiment, two or more morphological features are extracted and used from the NSR complexes in developing the NSR template. For example, four features can be extracted from each NSR complex in developing the NSR template. In one embodiment, the features have a numerical value which are characteristic of the morphological position along the cardiac complex. So, at 310, as the NSR complexes are sensed, a set of four features are extracted, and a four feature NSR complex is created and stored for each of the NSR complexes. FIG. 4 shows one embodiment of a NSR complex 400. The NSR complex 400 is processed to determine the amplitudes of peaks 402 and valleys 404 in the QRS-complex 406. In one embodiment, the peaks 402 and valleys 404 are determined by determining major inflection points in the QRS-complex as represented in FIG. 4. The resulting values of the peaks 402 and valleys 404 provide a four dimensional NSR complex vector, [1A, 1B, 1C, 1D], where the number "1" represents the number of the sensed NSR complex. As previously mentioned, other features from cardiac complexes known in the art can be used in developing vectors. By way of example, other features can include the start or ending of a cardiac complex as detected by a predetermined deviation from a baseline signal or by detecting a predetermined decrease or increase in the slope of the cardiac signal. Thus, the present subject matter is in no way limited to vectors developed from maximum and minimum deflection points along signals of cardiac complexes.

Referring again to FIG. 3, at 320, a NSR template is determined from a plurality of the NSR complex vectors. In one embodiment, the NSR template is a median value computed from the corresponding NSR complex vectors. For example, the NSR template [TA, TB, TC, TD] is determined from a series of NSR complex vectors [1A, 1B, 1C, 1D], [2A, 2B, 2C, 2D], [3A, 3B, 3C, 3D]where TA equals the median value of (1A, 2A, 3A, ... nA), TB equals the median value of (1B, 2B, 3B, ... nB), TC equals the median value of (1C, 2C, 3C, ... nC), and TD equals the median value of (1D, 2D, 3D ... nD). In an alternative embodiment, the NSR template feature value is an average value computed from the corresponding NSR complex vectors. The number of NSR complexes used in determining TA, TB, TC, TD is a programmable value. In one embodiment, the number of NSR complexes used in determining the NSR template is a programmable value in the range of 10 to 100 NSR complexes.

At 330, the NSR template is used to create the matched filter impulse response (h(t)). In one embodiment, the matched filter impulse response is defined to be:

$h(t)=[TD, TC, TB, TA]$

The h(t) is "matched" to the NSR template. A matched filter is a specific type of filter designed to maximize the output signal-to-noise ratio. The matched filter effectively correlates an input signal with a stored replica of a signal of interest. The impulse response of the matched filter is the signal of interest time reversed and possibly time shifted. When a signal of interest is detected by the matched filter, the output signal-to-noise ratio will be maximized.

In one embodiment, the h(t) is used to filter features from tachycardia complexes sensed during a tachycardia event. In an additional embodiment, the system at 340 performs a numerical convolution of the NSR template and the NSR complexes to give a NSR filter output. The system at 350 then determines a NSR filter output template from the NSR filter output. In one embodiment, features are extracted from normal sinus rhythm complexes to create the NSR filter output template. In one embodiment, the features extracted from the NSR complexes create a four element vector as previously discussed. The extracted features are taken from the same relative position along the tachycardia complexes as the features taken from the NSR complexes. After extracting the features from the sensed tachycardia complexes, the feature values are stored for processing or filtering.

In one embodiment, as tachycardia complexes are sensed during a tachycardia event, the system extracts the values of the four features along the tachycardia complexes. In one embodiment, the values of the four features are referred to as vectors. As the vector is determined for each sensed tachycardia complex, the system filters the complex with respect to the four features of the normal sinus rhythm template. The result is a seven (7) element filter output for each of the sensed cardiac complexes.

In one embodiment, the vector for each of the NSR cardiac complexes are convolved with h(t). In one embodiment, this procedure produces the seven (7) element filter output for each of the sensed cardiac complexes. The seven element filter output values are then used to determine the NSR filter output template. In one embodiment, the NSR filter output template is a median value computed from a plurality of normal sinus rhythm complexes, where the median NSR filter output template has a median value for each value in the NSR filter output. For example, the median NSR filter output template [TE, TF, TG, TH, TI, TJ, TK] is determined from a plurality of NSR complex vectors [1E, 1F, 1G, 1H, 1I, 1J, 1K], [2E, 2F, 2G, 2K], [3E, 3F, 3G, 3H, 3I, 3J, 3K] ... , [nF, nG, nH, nI, nJ, nK], where TE equals median value of (1E, 2E, 3E, ... nE), TF equals the median value of (1F, 2F, 3F, ... nF), TG equals the median value of (1G, 2G, 3G, ... nG), TH equals the median value of (1H, 2H, 3H, ... nH), TI equals the median value of (1I, 2I, 3I, ... nI), TJ equals the median value of (1J, 2J, 3J, ... nJ), and TK equals the median value of (1K, 2K, 3K, ... nK). In an alternative embodiment, the NSR filter output template is an average value computed from the corresponding NSR complex vectors.

In one embodiment, the method for determining a normal sinus rhythm (NSR) template is performed with an implantable cardioverter defibrillator. The ICD system discussed herein is one example of an appropriate system for determining a patient's NSR template. In an alternative embodiment, other implantable medical devices, such as implantable defibrillators, or external defibrillators can be used to determine the NSR template and implement the present subject matter.

Figure 5:
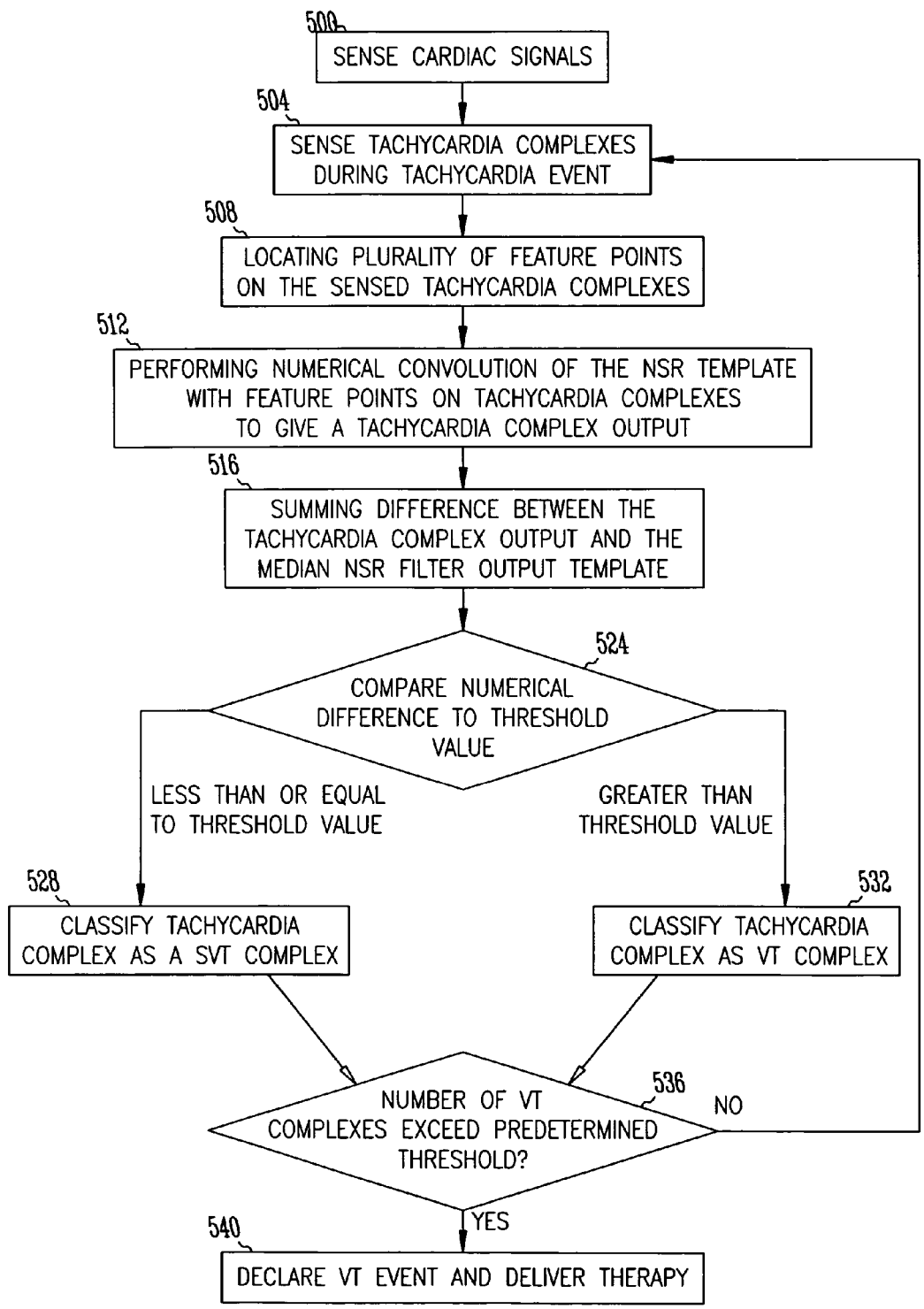
FIG. 5 is a flow chart illustrating one embodiment of the present subject matter.

FIG. 5 shows an embodiment of a system for distinguishing SVT events from VT events during a tachycardia event. At 500, cardiac signals representative of electrical cardiac activity are sensed. In one embodiment, the cardiac signals are sensed by an endocardial lead system of an ICD as previously discussed. The cardiac signals include cardiac complexes which are portions of the complete cardiac cycles. In one embodiment, the sensed cardiac complexes include the QRS-complex of the cardiac cycle. The system analyzes the sensed cardiac complexes to determine if a tachycardia event is occurring. In one embodiment, the system determines the occurrence of a tachycardiac event by analyzing the sensed cardiac rate. A cardiac rate that exceeds a predetermined threshold indicates the occurrence of a ventricular tachycardia. In one embodiment, the predetermined threshold is for cardiac rates of between 150–250 beats per minute. In an alternative embodiment, the predetermined threshold is a lower rate zone in an ICD that is configured with multiple rate-zones. Other methods of determining the occurrence of tachycardia event which are known in the art may be used without departing from the present system.

When a tachycardia event is detected, the system proceeds to 504. At 504, the system samples the tachycardia complexes during the tachycardia event. Feature points along the tachycardia complexes are located on the QRS-complex of the tachycardia complexes at 508. In one embodiment, the feature points located along the sensed tachycardia complexes are at the same relative position as feature points located along QRS-complexes sensed during normal sinus rhythm. For example, the QRS-complex is isolated, or windowed, for analysis and vector values derived for the complex as previously discussed.

In one embodiment, the set of features extracted from the QRS-complex of the cardiac complex are processed using the NSR template. In one embodiment, the set of features extracted from the QRS-complex are convolved with the matched filter impulse response (h(t)) of the NSR template at 512 to give a tachycardia complex output. In one embodiment, the h(t) used at 512 is derived from features extracted from a patient's normal sinus rhythm complexes.

In processing the tachycardiac complexes with h(t), the system extracts features from the morphology of the tachycardiac complexes. In one embodiment, the number of features extracted from the morphology signal of the tachycardiac complexes is equal to the number of features extracted from the morphology signals of the sensed normal sinus rhythm complexes. So, for example, four features are extracted from the morphology of the sensed normal sinus rhythm complexes and so four features are extracted from each of the sensed tachycardiac complexes. The extracted features are taken from the same relative position along the sensed tachycardiac complexes as those taken from the complexes sensed during normal sinus rhythm. After extracting the features from the sensed tachycardiac complexes, the feature values are stored for processing, or filtering (including the use of a matched filtering), with the normal sinus rhythm template at 512.

In one embodiment, as the tachycardiac complexes are sensed during the tachycardia event, the system measures values for each of the features along the tachycardiac complex. In one embodiment, the values of the features are referred to as vectors. As the vector values are determined for each sensed tachycardiac complex, the system filters the signal with respect to the features of the normal sinus rhythm template (or the matched filter impulse response) to give the tachycardia complex output. For example, when four features are sensed from the normal sinus rhythm complexes and the tachycardiac complexes, the system filters the tachycardiac complexes with respect to the four features of the normal sinus rhythm template (or matched filter impulse response). When four features are used, the result of the filtering process is a seven (7) element filter output for each of the sensed tachycardiac complexes. In this embodiment, the seven element filter output is the tachycardia complex output for the sensed cardiac complex.

In one embodiment, the filtering process is similar to a mathematical convolution of the normal sinus rhythm template with the features extracted from the sensed cardiac signals. In one embodiment, the process of numerical convolution can be envisioned as the interaction between two strips. In one embodiment, the numerical convolution of y(t)=f(t)*h(t) can be described where the sequence of f[1], f[2], f[3], ..., [samples for f(t)] are written on the upper strip, and the sequence h[1], h[2], h[3], ..., [samples for h(t)], are written on the lower strip. The upper strip is fixed, and the lower strip is folded (inverted) about t=1 and then moved from left to right, one slot at a time, with the f[1] and h[1] slots coinciding at t=1. To compute y(t), the lower strip is shifted by t slots and multiply the sample values of f(t) by the samples values of h(t) lying in the adjacent slots. The product of the multiplied samples are then summed together. This procedure is then repeated for each time the lower strip is shifted along the upper strip. For example, in filtering the four features of the cardiac complex for the present system, the result is a seven member vector (the tachycardia complex output for the sensed cardiac complex), where the seven member vector is determined from the calculation of:

[h(1)f(1), h(1)f(2)+h(2)f(1), h(1)f(3)+h(2)f(2)+h(3)f(1), h(1)f(4)+h(2)f(3)+h(3)f(2)+h(4)f(1), h(2)f(4)+h(3)f(3)+h(4)f(2), h(3)f(4)+h(4)f(3), h(4)f(4)]

At 516, the system then sums the difference between the tachycardia complex output and the median NSR filter output template. In one embodiment, the resulting difference is given the term sum of residuals (SOR) value. In one embodiment, a SOR value is calculated for each of the sensed tachycardiac complexes. One way to think of the SOR is as a differentiation value, where the SOR is used as a comparison of magnitudes at specific points along morphological signals. In one embodiment, the SOR is calculated from the seven-element output vectors from the sensed tachycardiac complexes and the normal sinus rhythm output template.

As the SOR can be thought of as the sum of differences between the tachycardia complex output and the median NSR filter output template, there are many ways in which the differences can be calculated. For example, the SOR is determined by taking the absolute value of the differences of corresponding elements from a seven-element output vector and the single, seven-element NSR output template. These quantities are then added together to produce a scalar quantity for each complex. This computation can also be described mathematically as:

$$\text{Sum of Residuals} = \sum_{i=1}^{7} |N_i - T_i|,$$

Where: N=seven-element NSR output template.
T=seven-element tachycardia output vector.

In an additional embodiment, the SOR value can also be calculated by determining the sum of the square of the differences between $N_i$ and $T_i$. Alternatively, the SOR value can be calculated by summing the difference between $N_i$ and $T_i$. Other mathematical methods of quantifying differences between $N_i$ and $T_i$ exist and are considered within the scope of the present invention.

Figure 6A:
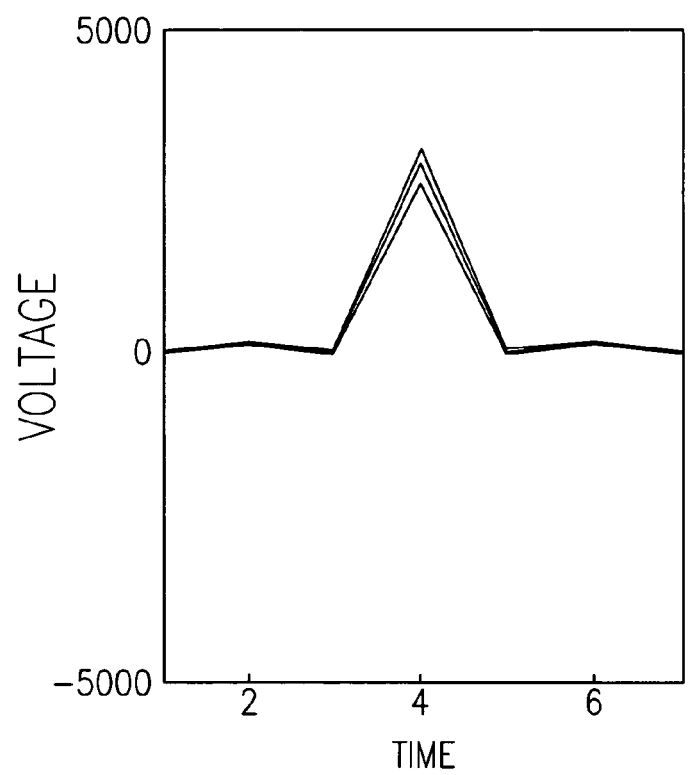
FIGS. 6A, 6B and 6C show plots of sensed cardiac complexes as a function of time for three cardiac conditions.
Figure 6B:
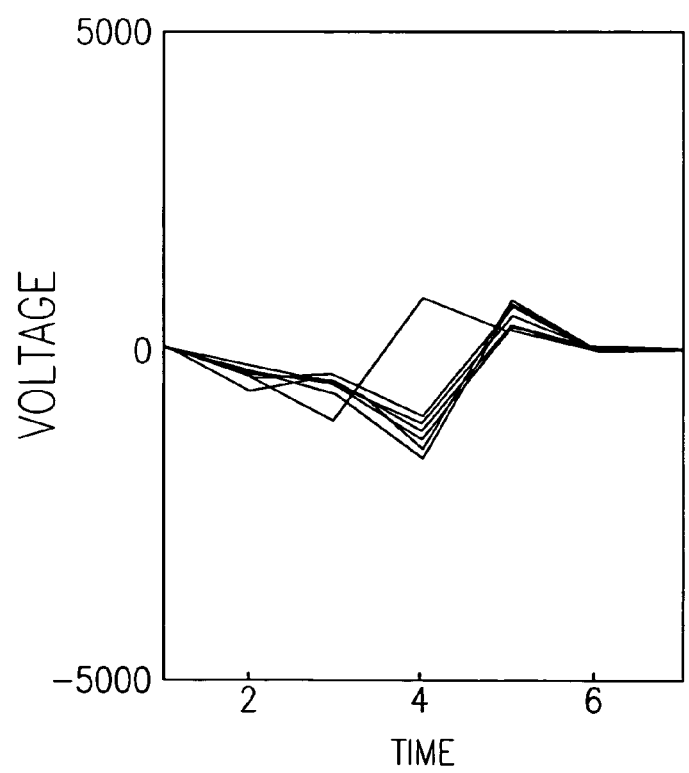
Figure 6C:
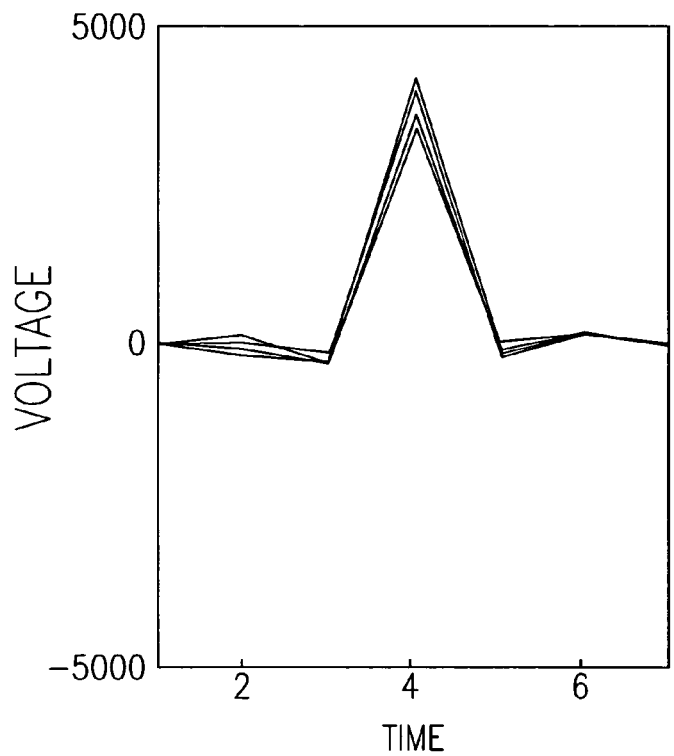

Referring now to FIGS. 6A, 6B and 6C there are shown sensed cardiac complexes plotted as a function of time. FIG. 6A shows cardiac complexes sensed during normal sinus rhythm; FIG. 6B shows cardiac complexes sensed during ventricular tachycardia; and FIG. 6B shows cardiac complexes sensed during atrial fibrillation.

Figure 6D:
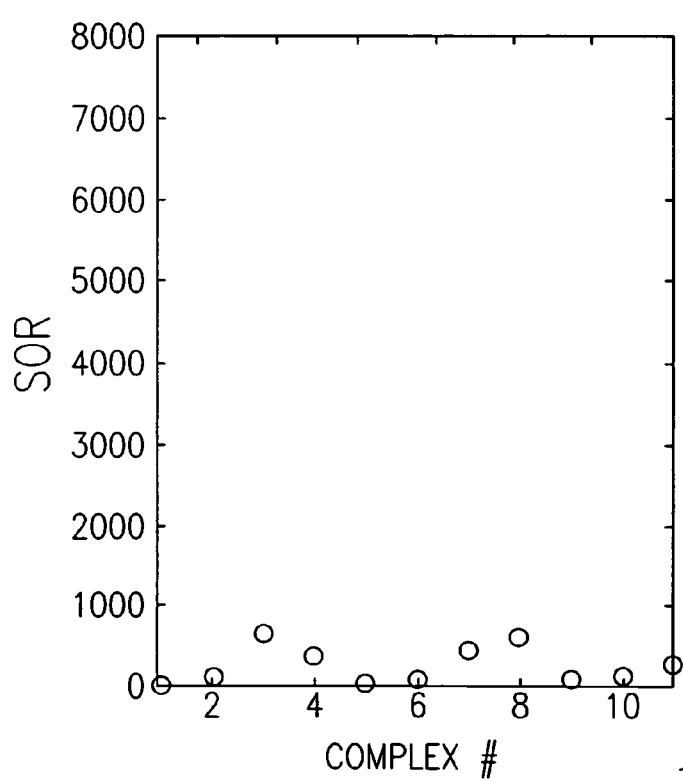
FIGS. 6D, 6E and 6F show plots of SOR values as a function of sensed cardiac complex for the sensed cardiac complexes of FIGS. 6A, 6B and 6C.
Figure 6E:
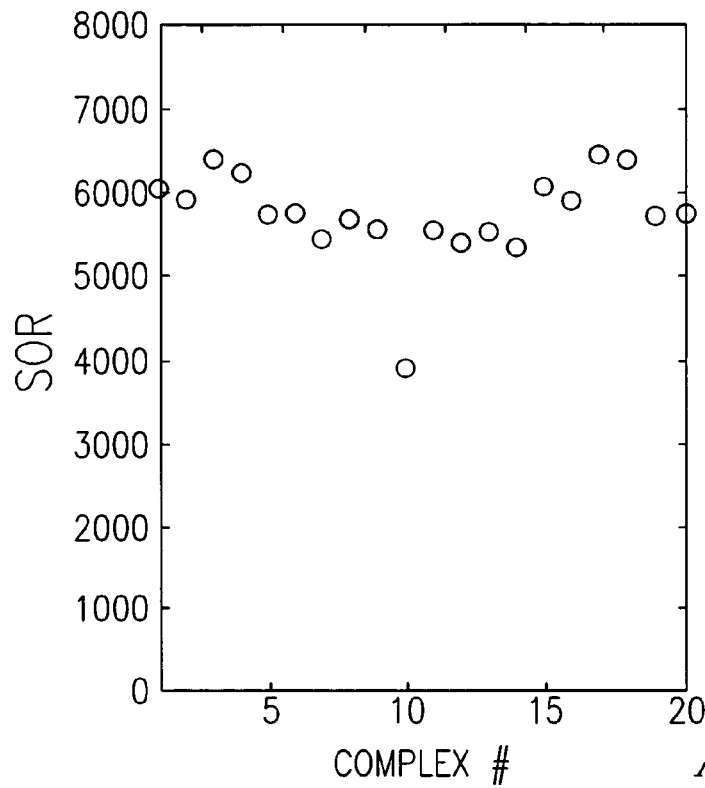
Figure 6F:
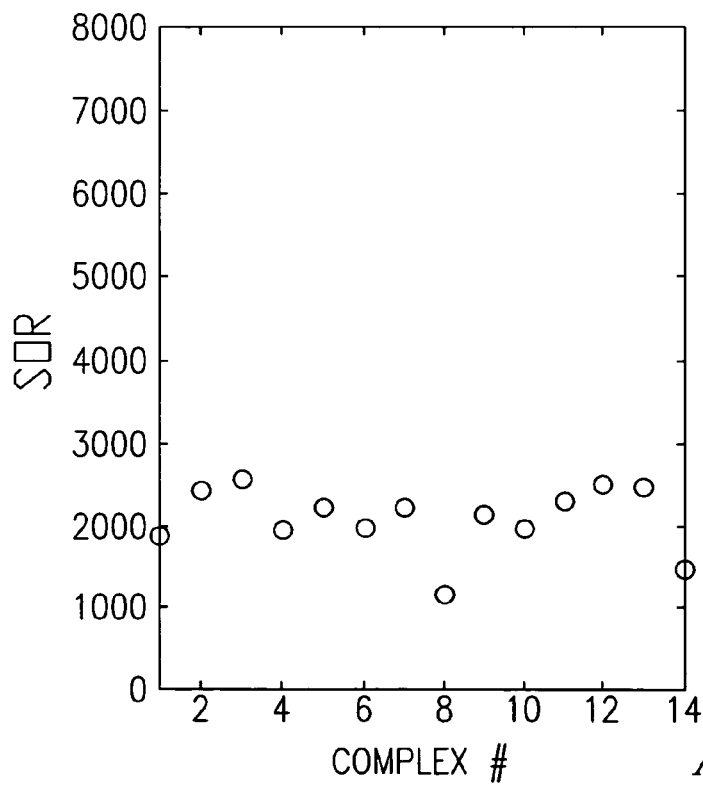

FIGS. 6D, 6E and 6F show SOR values plotted as a function of sensed cardiac complexes. FIG. 6D shows SOR values calculated for the cardiac complexes plotted in FIG. 6A; FIG. 6E shows SOR values calculated for the cardiac complexes plotted in FIG. 6B; and FIG. 6F shows SOR values calculated for the cardiac complexes plotted in FIG. 6C.

Comparing the calculated SOR values for each of FIGS. 6D, 6E and 6F reveal differences in SOR values for the cardiac complexes sensed during the ventricular tachycardia event and the atrial fibrillation event as compared to cardiac complexes sensed during normal sinus rhythm. Additionally, differences in SOR values can be seen for the cardiac complexes sensed during the ventricular tachycardia event as compared to those of the atrial fibrillation event.

Referring again to FIG. 5, after the sum of the differences between the tachycardia complex output and the median NSR filter output template is computed at 516, the system compares the numerical difference to a threshold value at 524. In one embodiment, the SOR value for each tachycardiac complexes is compared to a SOR threshold value. In one embodiment, when the numerical difference is less than the threshold value, the cardiac complex is classified as a supraventricular tachycardia (SVT) complex at 528. In one embodiment, when the numerical difference is greater than, or equal to, the threshold value, the cardiac complex is classified as a ventricular tachycardia (VT) complex at 532.

As the sensed tachycardiac complexes are categorized, the system records the number of ventricular tachycardia complexes and SVT complexes that have been categorized during the tachycardia event at 536. In one embodiment, the predetermined threshold is an x out of the last y signals counter. In one embodiment, the values for x and y are programmable. In one embodiment, x has programmable integer values of greater than 3, where the values can be in the range of 3 to 10, where, in an additional embodiment, 5 is an acceptable value. In one embodiment, y has a programmable integer value of greater than 8, where the values can be in the range of 8 to 30, where 10 is an acceptable value. In an alternative embodiment, the system determines a percentage of VT complexes during the tachycardia event. When the percentage of the VT complexes exceeds a predetermined percentage threshold, the system declares the occurrence of a ventricular tachycardia. In one embodiment, the predetermined percentage threshold is a programmable value in the range of 30 to 100 percent, where 50 percent is an acceptable value.

When the number of VT complexes exceeds the predetermined threshold, a VT event is declared. A signal is then provided to the system (e.g., an implantable medical device) to deliver ventricular tachycardia therapy at 540 to a heart when a ventricular tachycardia episode is declared. In an alternative embodiment, if the number of SVT complexes exceeds the predetermined threshold, an SVT event is declared. In one embodiment, when an SVT event is declared, a signal is provided to the system (e.g., an implantable medical device) to deliver supraventricular tachycardia therapy to the heart. In an alternative embodiment, therapy is not delivered to the supraventricular region of the heart, but rather the system continues to monitor the cardiac condition and provides treatment only when a ventricular tachycardia is determined. If at 536 the number of classified cardiac complexes does not exceed the predetermined threshold, the system returns to 508 to sense and classify the next tachycardiac complex.

Figure 7:
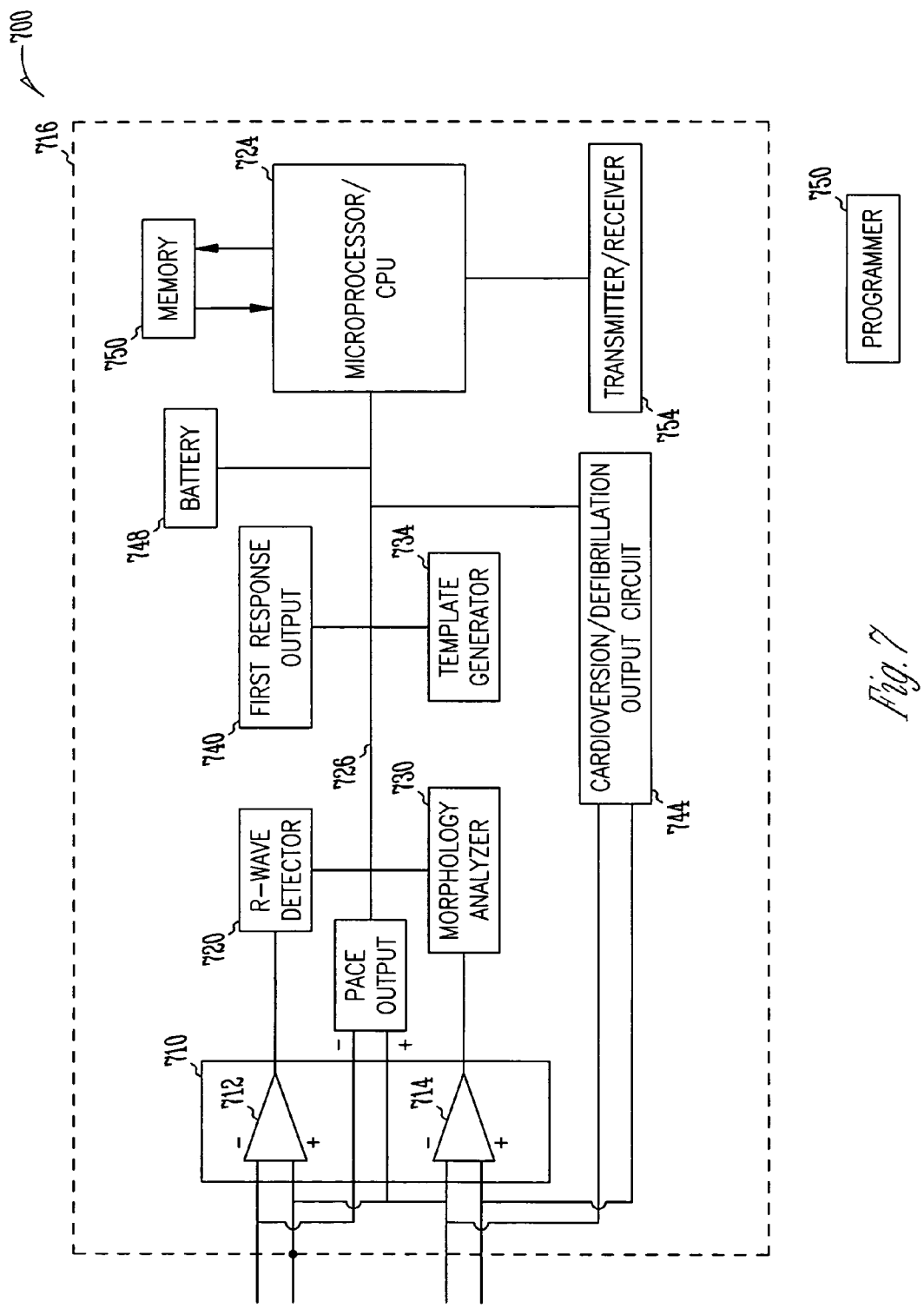
FIG. 7 is one embodiment of a block diagram of an implantable medical device according to the present subject matter.

FIG. 7 shows one embodiment of an implantable cardiac defibrillator (ICD) 700, which may include numerous defibrillation, pacing, and pulse generating modes known in the art. An endocardial lead is physically and electrically coupled to the ICD 700. The endocardial lead can include at least one pacing electrode and at least one defibrillation coil electrode as are known. In one embodiment, the endocardial lead is an ENDOTAK lead as previously described.

FIG. 7 discloses ICD 700 which includes input circuitry 710. In one embodiment, input circuitry 710 includes a first amp 712 and a second amp 714. The first amp 712 receives rate-signals or near-field signals through the at least one pacing electrode. In one embodiment, the rate-signals are sensed using a unipolar configuration, where the cardiac signals are sensed between the at least one pacing electrode and the housing 716 of the ICD 700. Alternatively, bipolar sensing is accomplished between two or more pacing electrodes on one or more endocardial leads. The second amp 714 receives morphology-signals, or far-field signals, from at least two defibrillation coil electrodes located on the endocardial lead.

An R-wave detector 720 receives the rate-signals from the first amp 712. The R-wave detector 720 detects R-waves from the rate-signals being received by the first amp 712 and conveys information relating to the cardiac rate to a microprocessor 724 by a data bus 726. A morphology analyzer 730 receives morphology signals from the second amp 714. In one embodiment, the morphology analyzer 730 extracts a plurality of feature points from sensed cardiac complexes. A template generating circuit 734 is coupled to the signal morphology analyzing circuit 730 by the bus 726. The template generating circuit 734 receives the extracted plurality of feature points. In one embodiment, the template generating circuit 734 generates a normal sinus rhythm template from sensed normal sinus rhythm complexes.

A filter output response circuit 740 is coupled to the template generating circuit 734 by bus 726. The filter output response circuit 740 creates a normal sinus rhythm filter output by performing a numerical convolution on the NSR template and the plurality of feature points for each of the plurality of the NSR complexes. The filter output response circuit 740 also determines a median normal sinus rhythm output template from the plurality of normal sinus rhythm complexes, where the median NSR filter output template has a median value for each value in the NSR filter output.

In one embodiment, when, during a tachycardia event, the input circuitry 710 receive a QRS-wave signal from a tachycardia complex, the signal morphology analyzing circuit 730 locates the plurality of feature points on the QRS-complex based on morphological features of the QRS-complex. The filter output response circuit 740 then performs a numerical convolution of the NSR template with the plurality of feature points on the QRS-complex to give a tachycardia complex output. The filter output response circuit 740 then sums a numerical difference between the values of the tachycardia complex output and the median NSR filter output template.

The summed difference is then received by the microprocessor 724 where the calculated value is compared to the predetermined sum of residual threshold value. During a tachycardia episode, as the system senses each cardiac complex the ICD 700 classifies each sensed cardiac complex as either being a ventricular tachycardia complex or a supraventricular complex. The ICD 700 then determines whether the number of ventricular tachycardia complexes exceeded a predetermined threshold value. In one embodiment, when the number of ventricular tachycardia complexes exceeded a predetermined threshold value, the ICD 700 declares a ventricular tachycardia event. When a ventricular tachycardiac event is declared, the microprocessor 724 provides a signal to a cardioversion/defibrillation output circuit 744 to deliver ventricular tachycardia therapy to a heart.

In an alternative embodiment, the ICD 700 determines whether the number of supraventricular tachycardia complexes exceeded the predetermined threshold value. In one embodiment, when the number of supraventricular tachycardia complexes exceeded a predetermined threshold value, the ICD 700 declares a supraventricular tachycardia event. When a supraventricular tachycardiac event is declared, the microprocessor 724 provides a signal to a cardioversion/ defibrillation output circuit 744 to deliver supraventricular tachycardia therapy to a heart.

Power to operate the ICD 700 is supplied by a battery 748. Memory 750 is also provided in the ICD 700, and is connected with the microprocessor 724. The ICD 700 further includes a transmitter/receiver 754, which can be used to communicate with the microprocessor 724 through a programmer 760 as is known.

The embodiments provided herein are intended to demonstrate only some of the embodiments of the present system. Other embodiments utilizing the present subject matter can be appreciated by those skilled in the art. For example, the concepts of the present subject matter are expressly described in terms of cardiac complexes sensed for the QRS-wave of the heart, however, applications to other cardiac complexes, including P-wave complexes or a combination of QRS-wave and P-wave complexes, can be readily appreciated by those skilled in the art without departing from the present invention.

Also, a dual chamber implantable cardiac defibrillator can be used to distinguish VT events from SVT events based on sensed cardiac signals. In one embodiment, the dual chamber implantable cardiac defibrillator includes an ENDOTAK single body lead catheter implanted in the ventricular region of the heart and an atrial catheter implanted in a supraventricular region of the heart. This embodiment allows for ventricular near-field signals and ventricular far-field signals, along with atrial near-field signals to be sensed and analyzed by the implantable cardiac defibrillator.

Other cardiac defibrillator systems and catheter configurations may also be used without departing from the present system. In addition to ICD systems, the present system may be utilized in external defibrillation systems and in external cardiac monitoring systems. In addition to employing endocardial leads, the present system can also utilize body surface leads.

Additionally, even though ventricular tachycardia events were discussed herein, other arrhythmic events can also be analyzed to determine the nature, or origin, of the cardiac arrhythmia using the teachings provided herein, and therefore, the express teachings of this disclosure are not intended in an exclusive or limiting sense.

What is claimed is:

1. A system, comprising:
    means for sampling a normal sinus rhythm (NSR) QRS-complex from a NSR cardiac cycle;
    means for locating a plurality of feature points on the NSR QRS-complex based on morphological features of the NSR QRS-complex;
    means for determining a NSR template for a plurality of the NSR cardiac cycles, wherein the NSR template includes a median value for each of the plurality of feature points;
    means for producing a NSR filter output from a numerical convolution of the NSR template and the plurality of feature points for each of the plurality of the NSR cardiac cycles;
    means for determining a median NSR filter output template for the plurality of the NSR cardiac cycles, wherein the median NSR filter output template has a median value for each value in the NSR filter output;
    means for detecting a tachycardia event;
    means for sampling a QRS-complex from a tachycardia complex during the tachycardia event;
    means for locating the plurality of feature points on the QRS-complex from the tachycardia complex based on morphological features of the QRS-complex;
    means for producing a tachycardia complex output from a numerical convolution of the NSR template with the plurality of feature points on the QRS-complex from the tachycardia complex;
    means for summing a numerical difference between the values of the tachycardia complex output and the median NSR filter output template; and
    means for classifying the tachycardia complex as a ventricular tachycardia complex when the sum of the difference between the values of the tachycardia complex output and the median NSR filter output template is greater than or equal to a predetermined sum of residual threshold value.

2. The system of claim 1, wherein the means for classifying the tachycardia complex comprises:
    means for determining an absolute value of the difference between the values of the tachycardia complex output and the median NSR filter output template; and
    means for classifying the cardiac complex as a supraventricular tachycardia complex when the absolute value of the difference between the values of the tachycardia complex output and the median NSR filter output template is less than the predetermined sum of residual threshold value.

3. The system of claim 2, further comprising:
    means for sampling a plurality of tachycardia complexes and classifying each of the plurality of tachycardia complexes as either a ventricular tachycardia complex or a supraventricular tachycardia complex; and
    means for determining whether a number of classified ventricular tachycardia complexes exceeds a predetermined threshold value.

4. The system of claim 3, further comprising means for declaring a ventricular tachycardia event when the number of ventricular tachycardia complexes exceeded the predetermined threshold value.

5. The system of claim 4, further comprising means for delivering a ventricular tachycardia therapy to a heart when the ventricular tachycardia event is declared.

6. The system of claim 3, further comprising means for declaring a supraventricular tachycardia event when the number of supraventricular tachycardia complexes exceeded the predetermined threshold value.

7. The system of claim 6, further comprising means for delivering a supraventricular tachycardia therapy to a heart when the supraventricular tachycardia event is declared.

8. A system, comprising:
    means for sampling a normal sinus rhythm (NSR) QRS-complex from a NSR cardiac cycle;
    means for locating a plurality of feature points on the NSR QRS-complex based on morphological features of the NSR QRS-complex;
    means for determining a NSR template for a plurality of the NSR cardiac cycles, wherein the NSR template includes a median value for each of the plurality of feature points;
    means for producing a NSR filter output from a numerical convolution of the NSR template and the plurality of feature points for each of the plurality of the NSR cardiac cycles;
    means for determining a median NSR filter output template for the plurality of the NSR cardiac cycles, wherein the median NSR filter output template has a median value for each value in the NSR filter output;
    means for detecting a tachycardia event;
    means for sampling a QRS-complex from a tachycardia complex during the tachycardia event;

means for locating the plurality of feature points on the QRS-complex from the tachycardia complex based on morphological features of the QRS-complex;

means for producing a tachycardia complex output from a numerical convolution of the NSR template with the plurality of feature points on the QRS-complex from the tachycardia complex;

means for summing a numerical difference between the values of the tachycardia complex output and the median NSR filter output template;

means for classifying the tachycardia complex as a ventricular tachycardia complex when the sum of the difference between the values of the tachycardia complex output and the median NSR filter output template is greater than or equal to a predetermined sum of residual threshold value; and means for classifying the cardiac complex as a supraventricular tachycardia complex when an absolute value of the difference between the values of the tachycardia complex output and the median NSR filter output template is less than the predetermined sum of residual threshold value.

9. The system of claim 8, further comprising:

means for declaring a ventricular tachycardia event when a number of ventricular tachycardia complexes exceeded a predetermined threshold value.

10. The system of claim 9, further comprising:

means for delivering a ventricular tachycardia therapy to a heart when the ventricular tachycardia event is declared.

11. The system of claim 10, wherein the means for delivering a ventricular tachycardia therapy includes an implantable pacemaker.

12. The system of claim 8, further comprising:

means for declaring a supraventricular tachycardia event when a number of supraventricular tachycardia complexes exceeded a predetermined threshold value.

13. The system of claim 12, further comprising:

means for delivering a supraventricular tachycardia therapy to a heart when the supraventricular tachycardia event is declared.

14. A system, comprising:

means for sampling a normal sinus rhythm (NSR) QRS-complex from a NSR cardiac cycle;

means for locating a plurality of feature points on the NSR QRS-complex based on morphological features of the NSR QRS-complex;

means for determining a NSR template for a plurality of the NSR cardiac cycles, wherein the NSR template includes a median value for each of the plurality of feature points;

means for producing a NSR filter output from a numerical convolution of the NSR template and the plurality of feature points for each of the plurality of the NSR cardiac cycles;

means for determining a median NSR filter output template for the plurality of the NSR cardiac cycles, wherein the median NSR filter output template has a median value for each value in the NSR filter output;

means for detecting a tachycardia event;

means for sampling a QRS-complex from a tachycardia complex during the tachycardia event;

means for locating the plurality of feature points on the QRS-complex from the tachycardia complex based on morphological features of the QRS-complex;

means for producing a tachycardia complex output from a numerical convolution of the NSR template with the plurality of feature points on the QRS-complex from the tachycardia complex;

means for summing a numerical difference between the values of the tachycardia complex output and the median NSR filter output template;

means for classifying the tachycardia complex as a ventricular tachycardia complex when the sum of the difference between the values of the tachycardia complex output and the median NSR filter output template is greater than or equal to a predetermined sum of residual threshold value; and means for sampling a plurality of tachycardia complexes and classifying each of the plurality of tachycardia complexes as either a ventricular tachycardia complex or a supraventricular tachycardia complex.

15. The system of claim 14, wherein the means for summing a numerical difference includes a microprocessor.

16. The system of claim 15, further comprising an output circuit coupled to the microprocessor, wherein the output circuit is adapted to deliver cardioversion and defibrillation therapy.

17. The system of claim 14, wherein the means for detecting a tachycardia event includes an input circuit.

18. The system of claim 14, wherein the means for locating the plurality of feature points includes a morphology analyzing circuit.

19. The system of claim 14, wherein the means for producing a tachycardia complex output includes a filter output response circuit.

20. The system of claim 14, wherein the means for classifying the tachycardia complex includes a microprocessor.

* * * * *